United States Patent [19]
Herald, Jr. et al.

[11] Patent Number: 5,657,106
[45] Date of Patent: Aug. 12, 1997

[54] SAFETY GOGGLE ASSEMBLY INCLUDING CORRECTIVE LENSES

[75] Inventors: A. Glen Herald, Jr., Collierville, Tenn.; John Chin, Tainan, Taiwan

[73] Assignee: Crews, Inc., Memphis, Tenn.

[21] Appl. No.: 552,688

[22] Filed: Nov. 3, 1995

[51] Int. Cl.⁶ .................... G02C 7/08; G02C 11/08; A61F 9/02
[52] U.S. Cl. .................. 351/57; 351/62; 351/158; 2/437; 2/443
[58] Field of Search .................. 351/41, 57–58, 351/62, 140, 155, 158; 2/437, 438, 442, 443, 444, 445, 446

[56] References Cited

U.S. PATENT DOCUMENTS 5,069,541  12/1991  Holmes et al. ............... 351/57
5,410,763  5/1995   Bollé ......................... 2/444

*Primary Examiner*—Huy Mai
*Attorney, Agent, or Firm*—Edwin E. Greigg; Ronald E. Greigg

[57] ABSTRACT

A safety goggle assembly in combination with a pair of glasses including corrective lenses. The safety goggles have at least one lens formed of a safety type material. The corrective glasses have at least one lens in a frame in which the frame is form with a bridge portion that fits tightly over a bridge of the goggle. The corrective glasses include an upper bar which fits behind a protruding member in a forehead portion of the goggle. Therefore, the corrective glasses will be secured within the goggle between the bridge and the forehead portion without the use of special securing elements.

17 Claims, 3 Drawing Sheets

SAFETY GOGGLE ASSEMBLY INCLUDING CORRECTIVE LENSES

BACKGROUND OF THE INVENTION

This invention is directed to safety goggles in which corrective lenses set in a frame are held within the safety goggle assembly without the use of special attachments or accessory elements.

Heretofore safety glasses in combination with corrective lenses have been set forth in the prior art. Safety goggles with corrective lenses in a frame have been set forth in U.S. Pat. Nos. 3,146,295 and 5,371,555. These are cumbersome assemblies and require special or accessory means for securing the corrective lenses within the goggle assembly.

SUMMARY OF THE INVENTION

The upper portion of the inventive goggle includes air vent elements. These air vents are positioned close relative to the front lens of the goggle such that a narrow gap is formed between an inner surface of the goggle near the front lens and the air vents. This narrow gap serves to confine a top portion of the corrective lens frame and provides an upper support in which a top bar on the lens frame fits in order to retain the upper edge of the frame positively. The inner wall surface of the nose bridge portion of the goggles is provided with an upstanding tang in which the bottom edge of the corrective lens frame fits in order to support the bottom portion of the lens frame within the goggle.

OBJECTS OF THE INVENTION

It is therefore an object of the invention to provide a safety goggle including corrective lenses in which the corrective lenses are mounted within the goggle assembly without the use of any accessory mounting means. The use of the term "corrective lenses" is meant to imply a pair of corrective lenses disposed in a frame, not just corrective lenses separately.

Another object is to provide a safety goggle in which corrective lenses can be assembled very easily and without any special tools.

Still another object is to provide a safety goggle within which corrective lenses can be mounted without any interference with the wearability of the goggles.

The invention will be better understood and further objects and advantages thereof will become more apparent from the ensuing detailed description of a preferred embodiment taken in conjunction with the drawings.

DETAILED DESCRIPTION OF THE DRAWINGS

Figure 1:
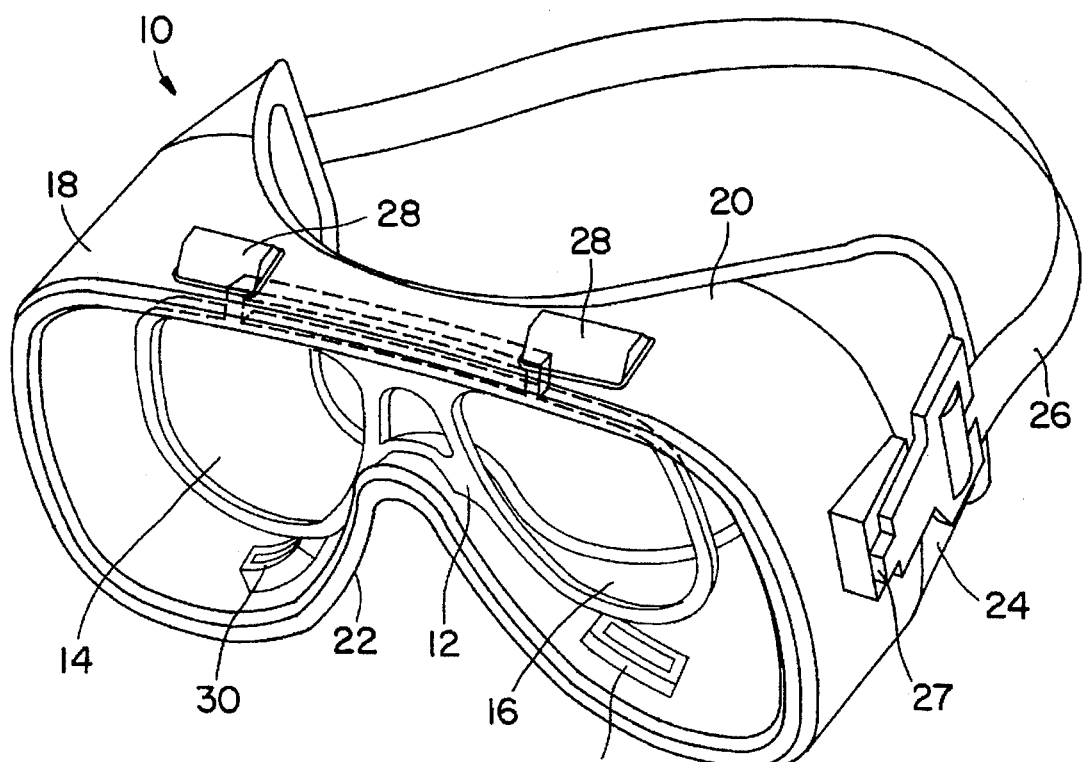
FIG. 1 illustrates a perspective view of a safety goggle with corrective lenses mounted within the goggles.
Figure 2:
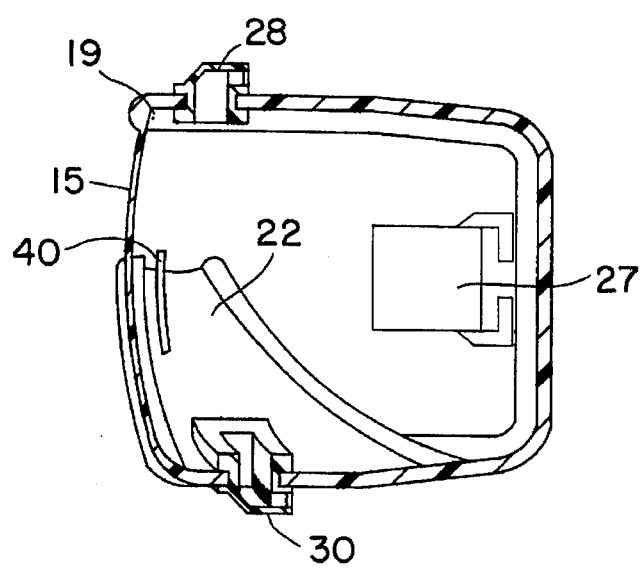
FIG. 2 is a cross-sectional view of the safety goggles illustrating a portion of the frame, upper and lower air vents and the nose bridge portion.
Figure 3:
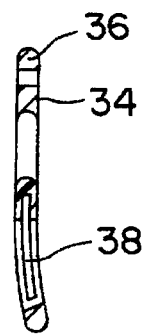
FIG. 3 is a cross-sectional view of a corrective lens.

FIG. 1 illustrates a perspective view of a safety goggle assembly 10 with a corrective lens frame 12 including corrective lenses 14 and 16 mounted within the goggle assembly. As shown, the safety goggle has a so called wrap-around body member 18 which has a curved flexible surface to fit the face along the forehead portion 20 and nose bridge portion 22 and includes side extensions 24 to which a strap 26 is secured on opposite sides of the face by a strap connector 27. The safety goggle includes air vents 28 on the upper portion above the lenses and air vents 30 on the lower portion on opposite sides of the nose bridge 22. The safety goggle assembly can be made of any suitable plastic material, such as polyvinyl-chloride, which is flexible but has memory. The goggle lens 15 is shown as one piece and can be made of any suitable safety type material that will not break easily or shatter if broken. A suitable material is polycarbonate. The lens frame is preferably rigid and made of nylon or polycarbonate.

Figure 4:
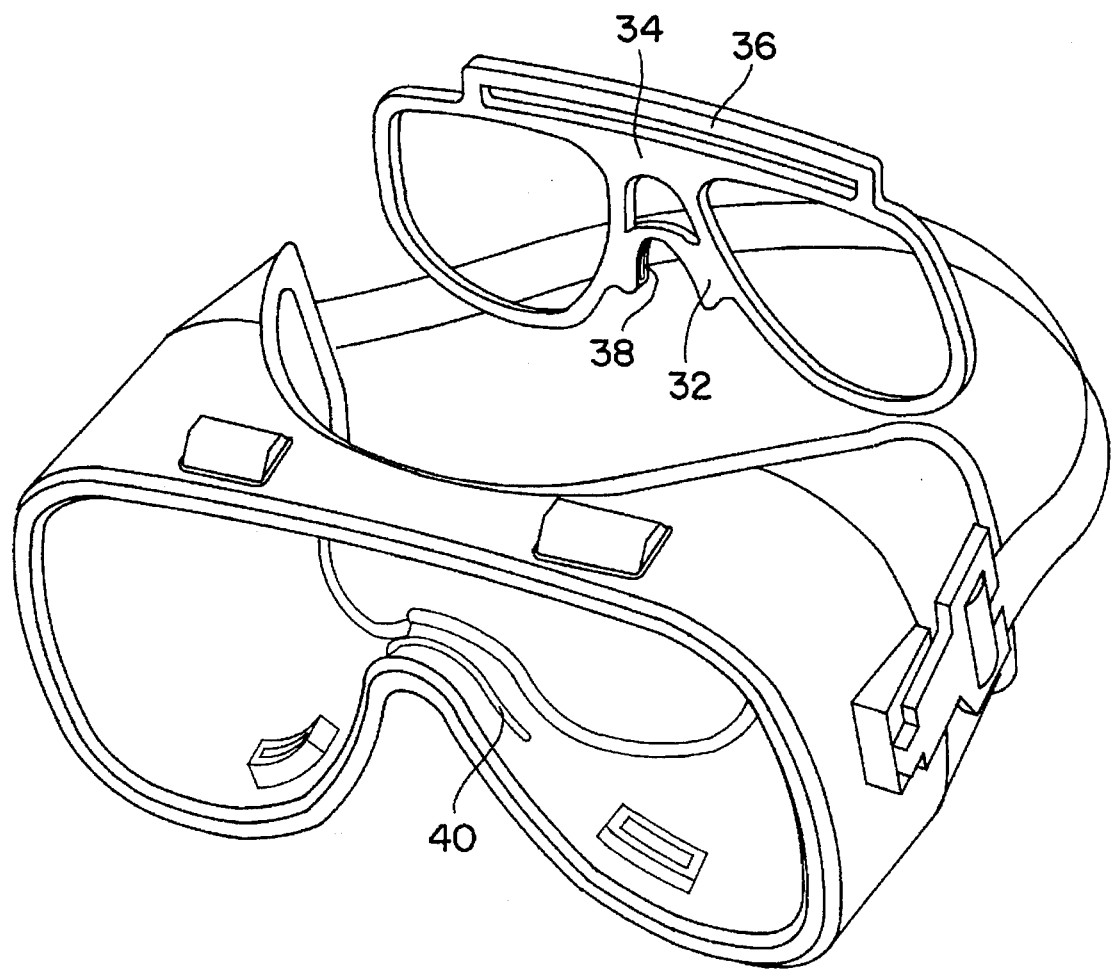
FIG. 4 illustrates a perspective view of the safety goggle with the corrective lenses shown removed from the goggle assembly.

As shown, the safety goggle includes corrective lenses 14 and 16 mounted within a frame 12. The corrective lenses should be of a type which will not shatter if broken. Any suitable material may be used for the lenses 14, 16. The corrective lens frame is formed as one piece having a bridge portion 32 which has a shape to fit over the bridge portion of the safety goggle with a tight fit. As best shown in FIG. 4, the frame has an upper frame portion 34 above which a top bar or securing strip 36 is formed integral with the frame. The corrective lens frame requires no temples or any other parts; it consists only of the bridge frame including the upper bar and the corrective lens.

Figure 5:
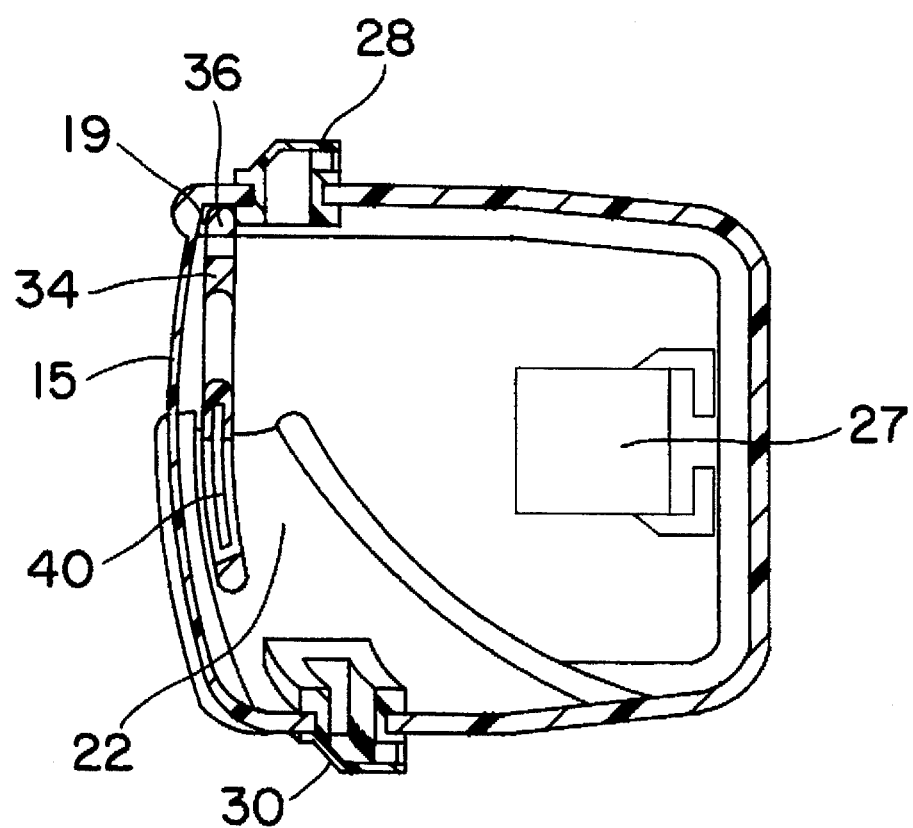
FIG. 5 is a cross sectional view of the safety goggle and corrective lens frame held in place as an assemblage within the safety goggle.

Any suitable safety goggle assembly can be used which includes a nose bridge portion and means on the upper forehead portion along which the upper bar 36 can be secured. In the Safety goggles shown, the bridge of the corrective lens fits over the nose bridge portion of the safety goggles and the upper bar of the corrective lens fits adjacent to the front surface of the upper air vents as shown in FIG. 5.

In assembly of the corrective lens frame within the goggle, a curved groove or slot 38 in the interior of the nose bridge of the frame is placed on an upstanding complementally shaped curved tang 40 formed on the bridge of the goggle, the goggle forehead portion is then flexed outwardly, and then the upper bar 36 is slipped into place in front of the upper air vents where it is held between the front vent surface and the goggle peripheral edge 19. The forces gripping the upper bar 36 between the air vents and the goggle and that provided by the groove and tang on the nose bridge of the frame for the corrective lenses will secure the corrective lenses within the safety goggle.

In order to remove the corrective lens, the goggle is flexed slightly to allow the bar on the frame to be pulled from behind the air vents and the bridge to be lifted off of the cooperating tang.

In use of safety goggles as set forth herein, any person with corrective lens in an appropriate frame can use the safety goggle by inserting their own corrective lens and frame combination into the safety goggle to form an assembly. Thus, the safety goggle can be used by any number of persons, one at a time, such that one could purchase a set number of safety goggles for use by a much greater number of persons that require corrective lenses. For example, a safety goggle for each station of an assembly line which operates on multiple shifts. Each person would have their own corrective lens with the frame formed to fit within the safety goggle as set forth above.

The foregoing relates to preferred exemplary embodiments of the invention, it being understood that other variants and embodiments thereof are possible within the spirit and scope of the invention, the latter being defined by the appended claims.

What is claimed:

1. A frame for supporting at least one corrective lens for use in safety goggles in which said frame comprises a nose bridge having a shape complemental to a nose bridge portion of said safety goggle, first means (36) that forms an upper linear bar along a portion of said corrective lens frame by which said upper portion of said corrective lens frame is secured within a support means (19) within a forehead portion of said safety goggle juxtaposed a lens in said safety goggle and second means (32) of said corrective lens frame which fits in an area above said nose bridge portion of said safety goggle juxtaposed said lens in said safety goggle, said first and second means together are adapted to retain said frame tightly in place within said support means and above said nose bridge of said goggle.

2. A frame as set forth in claim 1, wherein said safety goggles comprise a tang upstanding from said area above the nose bridge portion of the safety goggle and said frame includes a cooperating slot (38) in an underside portion of a nose bridge of said frame.

3. A frame as set forth in claim 2, wherein said corrective lens frame includes two separate lenses.

4. A frame as set forth in claim 2, wherein at least one lens is a corrective lens.

5. A frame as set forth in claim 3, wherein said two separate lenses are corrective lenses.

6. A safety goggle assembly in combination with a corrective lens frame which includes at least one corrective lens, said safety goggle includes a housing having a forehead portion, a nose bridge portion, and protective side portions, a lens frame for holding at least one safety lens in said lens frame of said goggle, projecting means on said forehead portion of said goggle which project into an inner area of said housing to form a goggle peripheral edge (19) which is spaced from said lens frame of said goggle, said corrective lens frame including an opening in which at least one corrective lens is secured, a nose bridge portion having a shape of an inner surface of said nose bridge portion of said safety goggle housing, an upper surface (34) of said corrective lens frame which is shaped to conform with an inner surface of said forehead portion of said safety goggle, and a bar means (36) which projects upperwardly from said upper surface of said corrective lens frame;

whereby said corrective lens frame can be slipped over said nose bridge portion and said bar means (36) that projects upwardly from the upper surface (34) of said corrective lens frame seats juxtaposed said goggle peripheral edge (19) on said forehead portion of said safety goggle housing to secure said corrective lens frame within said safety goggle assembly.

7. A safety goggle assembly in combination with a corrective lens frame which includes at least one corrective lens as set forth in claim 6, wherein said corrective lens frame includes two corrective lenses.

8. A safety goggle assembly in combination with a corrective lens frame which includes at least one corrective lens as set forth in claim 7, wherein said forehead portion of said goggle assembly includes spaced air vents.

9. A safety goggle assembly in combination with a corrective lens frame which includes at least one corrective lens as set forth in claim 7, wherein said safety goggle assembly includes air vents (30) on a lower portion of said safety goggle assembly on opposite sides of said nose bridge.

10. A safety goggle assembly in combination with a corrective lens frame which includes at least one corrective lens as set forth in claim 6, wherein said bar means which projects upwardly from an upper surface (34) of said corrective lens frame is a linear bar (36).

11. A safety goggle assembly in combination with a corrective lens frame which includes at least one corrective lens as set forth in claim 10, wherein said is forehead portion of said goggle assembly includes spaced air vents.

12. A safety goggle assembly in combination with a corrective lens frame which includes at least one corrective lens as set forth in claim 10, wherein said safety goggle assembly includes air vents (30) on a lower portion of said safety goggle assembly on opposite sides of said nose bridge.

13. A safety goggle assembly in combination with a corrective lens frame which includes at least one corrective lens as set forth in claim 10, wherein said linear bar is integral with and includes a portion which is spaced from said upper surface of said corrective lens frame.

14. A safety goggle assembly in combination with a corrective lens frame which includes at least one corrective lens as set forth in claim 13, wherein said forehead portion of said goggle assembly includes spaced air vents.

15. A safety goggle assembly in combination with a corrective lens frame which includes at least one corrective lens as set forth in claim 13, wherein said safety goggle assembly includes air vents (30) on a lower portion of said safety goggle assembly on opposite sides of said nose bridge.

16. A safety goggle assembly in combination with a corrective lens frame which includes at least one corrective lens as set forth in claim 6, wherein said forehead portion of said goggle assembly includes spaced air vents.

17. A safety goggle assembly in combination with a corrective lens frame which includes at least one corrective lens as set forth in claim 6, wherein said safety goggle assembly includes air vents (30) on a lower portion of said safety goggle assembly on opposite sides of said nose bridge.

* * * * *